United States Patent
Svensson et al.

(10) Patent No.: US 6,333,007 B1
(45) Date of Patent: Dec. 25, 2001

(54) PHOTOMETER AND CUVETTE FOR MIXING

(75) Inventors: Johnny Svensson, Ängelholm; Bertil Nilsson, Bjärred; Per Olsson, Munka Ljungby; Lars Jansson, Ängelholm; Bo Jönsson, Billeberga, all of (SE)

(73) Assignee: Hemocue AB, Ängelholm (SE)

( * ) Notice: Subject to any disclaimer, the term of this patent is extended or adjusted under 35 U.S.C. 154(b) by 0 days.

(21) Appl. No.: 09/612,484

(22) Filed: Jul. 7, 2000

Related U.S. Application Data

(63) Continuation of application No. PCT/SE99/00040, filed on Jan. 14, 1999.

(30) Foreign Application Priority Data

Jan. 14, 1998 (SE) .................................................... 9800072

(51) Int. Cl.⁷ .................................................... G01N 21/03
(52) U.S. Cl. .................... 422/57; 422/82.09; 436/165
(58) Field of Search ................. 422/57, 82.09; 436/164, 165; 356/440; 366/110–116, 128, 210–212

(56) References Cited

U.S. PATENT DOCUMENTS

| | | |
|---|---|---|
| 4,088,448 | 5/1978 | Lilja et al. . |
| 4,339,241 | 7/1982 | Stöcker . |
| 4,610,546 | 9/1986 | Intraub . |
| 4,936,687 | 6/1990 | Lilja et al. . |
| 5,247,345 | 9/1993 | Curtis . |
| 5,256,376 * | 10/1993 | Callan et al. .................... 422/102 |
| 5,300,779 * | 4/1994 | Hillman et al. .................... 250/341 |
| 5,658,723 | 8/1997 | Oberhardt . |
| 5,736,404 * | 4/1998 | Yassinzadeh et al. .................... 436/52 |

FOREIGN PATENT DOCUMENTS

| | | |
|---|---|---|
| 107783 | 8/1974 | (DE) . |
| 0018435 | 11/1980 | (EP) . |
| 0075605 | 4/1983 | (EP) . |
| 0287883 | 10/1988 | (EP) . |
| 0469097 | 1/1996 | (EP) . |
| 0803288 | 10/1997 | (EP) . |

* cited by examiner

Primary Examiner—Jeffrey Snay
(74) Attorney, Agent, or Firm—Burns, Doane, Swecker & Mathis, L.L.P.

(57) ABSTRACT

A photometer for determining the transmission of a liquid sample in a microcuvette (7, 20, 22) has a cavity for a capillary layer of the liquid sample with a free liquid surface extended transversely of the principal plane of the cavity. The cavity is initially prepared with a reagent to achieve a reaction, which affects the transmission of the liquid sample for indicating its contents of a predetermined substance. The photometer has a holder (6) for the microcuvette and measuring means (9, 10) for measuring the transmission of a bundle of rays directed towards the microcuvette. The cuvette holder (6) is mounted on bearings for vibration in a direction having a component, which extends in the plane of the free liquid surface and is parallel with the principal plane of the cavity, thereby achieving a mixing to accelerate the dissolution and the reaction.

10 Claims, 4 Drawing Sheets

PHOTOMETER AND CUVETTE FOR MIXING

This is a continuation of International Application No. PCT/SE99/00040, filed Jan. 14, 1999, that designates the United States of America and which claims priority for Swedish Application No. 9800072-2, filed Jan. 14, 1998.

The present invention relates generally to determining the transmission of a liquid sample in a microcuvette by means of a photometer, which has a holder for the microcuvette and measuring means for measuring the transmission of a bundle of rays directed towards the cuvette. The microcuvette has a cavity for a capillary layer of the liquid sample, which has a free liquid surface extended transversely of the principal plane of the cavity. More specifically, the cavity can be such that the free liquid surface of the liquid sample is formed in the actual cavity or in connection therewith. The cavity is initially prepared with a reagent to achieve a reaction, which affects the transmission of the liquid sample and enables determination of its contents of a predetermined substance.

Optical methods, such as absorption or transmission photometry, for quantitative determination of the concentration of a substance in a solution are well known and well documented.

Photometers for carrying out such quantitative determinations are also well known and usually have an optical part, a mechanical part and an electrical part. The optical part comprises a source of light with, for instance, a monochromator or an interference filter for generating a bundle of rays of light with a predetermined wavelength and a light detector, which generates an electric signal corresponding to the luminous energy in the transmitted bundle of rays. The mechanical part comprises a casing, in which the optical part is mounted, and a holder which is also arranged in the casing and intended for a sample which is to be measured in the photometer.

The electrical part, which is also suitably arranged in the casing, comprises the necessary circuits for controlling the source of light and handling the signal from the light detector as well as a unit for presenting measurement results. A microprocessor with instructions can be included as an essential element in the electrical part.

A photometer like the one above is disclosed in EP 0 469 097. This patent discloses a photometer for determining glucose in whole blood. The photometer is based on measurement at two different wavelengths. One of these constitutes the measurement wavelength and the other a compensation wavelength for e.g. increasing the safety in measurements on turbid samples. The design of the photometer is simple and robust.

Disposable microcuvettes are disclosed in, for instance, U.S. Pat. No. 4,088,448. These microcuvettes are intended for sampling of liquid, such as blood, mixing of the liquid sample with a reagent and direct optical analysis of the sample mixed with the reagent. The cuvette comprises a body with two parallel and preferably planar surfaces, which define an optical wavelength and are placed at a predetermined distance from one another to form a planar measuring cavity. The measuring cavity communicates with the surroundings outside the body via an inlet. Moreover, the measuring cavity has a predetermined volume and is designed such that the sample can enter by capillary force. A dry reagent is applied to the inner surface of the cavity.

Microcuvettes based on the invention according to U.S. Pat. No. 4,088,448 have been commercially successful to a considerable extent and are currently used for quantitative determination of, for instance, haemoglobin and glucose in whole blood. An important factor which has contributed to this success is that the time from sampling to response is very short. One reason for this period of time being very short is that the reagent compositions that are used for determination of haemoglobin and glucose are readily soluble in the small amount of blood that is sucked into the capillary cavity of the microcuvette. This results in a mixing with uniform distribution of the reagent components practically immediately. However, it has been found that these prior-art microcuvettes are not suitable for determining components that require reagents, which are not readily soluble and which therefore require a comparatively long period of time for dissolution. Even if, as suggested in U.S. Pat. No. 4,088,448, a mixing of sample and reagent is carried out while vibrating the microcuvette, the mixing is insufficient.

A method, which has been developed specifically for mixing a liquid and a reagent in the thin capillary layers that exist in microcuvettes, has been suggested in U.S. Pat. No. 4,936,687. In this method, use is made of small magnetic particles as means to accomplish the mixing, and the actual mixing operation is carried out by using outer magnets, which are specially designed and arranged and operated in a predetermined fashion. After the mixing procedure, the magnetic particles are separated from that part of the sample which is to be analyzed.

Although this method functions well for certain combinations of liquids and reagents, it is not particularly attractive from an industrial and commercial point of view since special arrangements and designs of magnets are necessary. The use of fine magnetic particles and the separation of these particles after the mixing step also require time and work, which makes this method complicated and comparatively expensive. Moreover, there is a risk of chemical obstruction of both samples and reagents.

Furthermore, EP 75 605 discloses a method for mixing in capillary liquid layers. According to this method, the mixing is carried out in a reaction vessel, which comprises two parallel plates between which the liquid samples which are to be analyzed are applied as a thin layer. The mixing is carried out by relative motion of the plates perpendicularly to their planes. This type of mixing, however, cannot be applied to microcuvettes of the type stated above since the two parallel surfaces thereof which define the measuring cavity are arranged at a predetermined distance from one another.

A simple and effective method for mixing of liquid and reagent in thin capillary layers, which is also suitable for less soluble reagents, would increase the number of determinations that can be carried out in microcuvettes. As a result, the microcuvettes could be attractive also for analyses which up to now could not be performed or for which there has previously been no interest.

According to one aspect of the present invention, a solution has been found to the problem of mixing in the thin liquid layer in a microcuvette by means of a specially designed photometer, which has the distinguishing features stated in appended claim 1. Preferred embodiments of the photometer are recited in the associated dependent claims.

The inventive photometer carries out a mixing process, which in itself constitutes a second aspect of the invention with the features that are evident from appended claim 7. Preferred embodiments of this mixing process are evident from the associated dependent claims.

According to a first aspect, the invention thus concerns a photometer for determining the transmission of a liquid sample in a microcuvette which has a cavity for a capillary layer of the liquid sample with a free liquid surface extended transversely of the principal plane of the cavity. Moreover the cavity is initially prepared with a reagent to achieve a reaction, which affects the transmission of the liquid sample for quantification of the contents of the liquid sample of a predetermined substance. The photometer has a holder for the cuvette and measuring means for measuring the transmission through the cuvette. According to the invention, the holder is mounted in bearings for vibration in a direction having a component, which is positioned in the plane of the free liquid surface and is parallel with the principal plane of the cavity. This component is preferably a main component of the vibrating direction, i.e. the vibration occurs essentially in the plane of the free liquid surface and essentially in parallel with the principal plane of the cavity. As a result, a relative quick mixing is achieved, thus accelerating the dissolution and the reaction.

This vibration causes the free liquid surface to perform a wave motion like an elastic membrane, the wavelength and amplitude of the wave motion being dependent on the frequency and magnitude of the vibration.

In a preferred embodiment, the vibration is accomplished by the cuvette holder being mounted in bearings for oscillation about a shaft which is essentially parallel with the direction of a bundle of rays directed towards the microcuvette by the measuring means. The principal plane of the cavity in a microcuvette supported by the cuvette holder can extend in the plane of oscillation or make an acute angle therewith (or generally, with the direction of vibration) by being tilted essentially about a radius to the axis of oscillation.

According to the second aspect, the invention concerns a method of carrying out mixing in a thin liquid layer, which is arranged between two essentially plane-parallel walls arranged at a capillary distance from one another. The mixing is carried out by subjecting the walls to a motion essentially in the plane of the liquid layer, balancing this motion against the capillary force exerted by the walls on the liquid, and selecting the interface between the sample and the surrounding medium so that it functions as an elastic membrane. Preferably, the indicated motion is an essentially reciprocating motion.

This method is well suited to accomplish mixing of sample and reagent in the thin liquid layers that exist in microcuvettes of the type indicated above. Fundamentally, however, the mixing method can be applied to all liquids in the form of thin layers between essentially parallel walls which are arranged at a capillary distance from each other.

The capillary force depends on the type of material of the walls, the type of sample including additives, if any, such as reagents, and the distance between the walls. The frequency and amplitude parameters of the motion must be balanced against the capillary force that is present in the individual case, and these parameters must be sufficient to provide mixing without any risk that part of the liquid escapes from the microcuvette, which may happen if the frequency/amplitude is too high. The upper limit of the length of the elastic membrane, i.e. of the interface of the sample towards the surrounding medium, such as air, is present in the case where the volume of the liquid sample is only limited by the parallel walls and is not enclosed in a cavity. The lower limit is determined experimentally on the basis of sample liquid, reagent, suitable beat frequency, cavity depth etc.

When the correct conditions for the motion are present, the interface serves as an elastic membrane which forces the chemical compounds in the sample liquid and a reagent composition, if any, which is dissolved or being dissolved, to move with the liquid motion, which results in a mixing of sample liquid and reagent in the thin liquid layer.

As stated above, the mixing method according to the present invention is suitable for mixing in disposable microcuvettes into which the sample is drawn in by capillary action.

Such a microcuvette generally comprises a body with a measuring cavity, whose boundary surfaces comprise two essentially parallel and preferably planar surfaces, which define an optical path through the microcuvette and are arranged at a predetermined distance from one another to determine the length of the optical path (path length) through the microcuvette. The measuring cavity has a predetermined volume and gap width and a capillary inlet connects the cavity with the surroundings outside the body. Under the action of capillary force, the sample is drawn into the measuring cavity through the inlet. A predetermined amount of dry reagent is arranged in the measuring cavity, e.g. applied to the surface of the cavity.

The volume of the cuvette may vary in the range $0.1 \mu l$–1 ml and the thickness of the thin layer may vary between 0.01 ml and 2.0 mm, preferably between 0.1 mm and 1.0 mm. The distance between the walls at the inlet or opening of the cuvette can preferably be between 0.01 mm and 1 mm and is preferably greater than the distance between the wall in the measuring cavity.

Even if any type of reagent can be applied in the cuvette, special advantages are achieved when using reagents which are comparatively difficult to dissolve, such as proteins and carbohydrates.

According to the present invention, the mixing is carried out by making the microcuvette with the liquid sample and the reagent move essentially in the plane of the layer during a period of time and at a speed which are sufficient to accomplish the desired mixing. The motion can be rotating, but a reciprocating motion is preferred. Any combination of these motions can also be used. An important feature of the new mixing method is that the motion is balanced against the capillary force so that the liquid sample does not flow out of the microcuvette. The capillary force is determined by the type of sample and the material of the walls of the microcuvette, and the balancing operation is preferably made experimentally. As indicated above, it is a critical feature that the interface between the sample and the surroundings is selected so that this interface can serve as an elastic membrane, in which case the motion should preferably also occur in or at least have a component in the plane of the interface. When using disposable microcuvettes, the interface between sample and air in the inlet will serve as an elastic membrane only on the condition that the length of this inlet is sufficient or if the microcuvette contains at least one more cavity which is essentially non-capillary and can form a further elastic membrane. In the latter case, the inlet of the cuvette need not be greater than the distance between the parallel walls of the measuring cavity, while in the former case, i.e. when the volume of the sample liquid only forms a continuous interface (a continuous membrane) against the surrounding medium (air), the length of the inlet should be at least 5, preferably 10 times greater than the depth of the liquid layer in the measuring cavity.

According to a preferred embodiment, the essentially non-capillary cavity is arranged adjacent to the capillary measuring cavity containing the dry reagent, and essentially in alignment with the inlet and the measuring cavity. When the liquid sample in this embodiment is drawn into the microcuvette and mixed according to the invention, the liquid in the measuring cavity and the medium, usually air, which is present in the non-capillary cavity form a separate interface which also serves as an elastic membrane.

An embodiment of a photometer according to the invention as well as microcuvettes used therewith will now be described in more detail with reference to the accompanying drawings, in which FIG. 1 is a perspective view of an embodiment of a photometer according to the invention in a closed position, FIG. 2 is a corresponding perspective view of the photometer in an open position, FIG. 3 is a top plan view of the photometer in FIG. 2, FIG. 4 is a cross-sectional view along line IV—IV in FIG. 3, FIG. 5 is a cross-sectional view in parallel with the top plan view in FIG. 3, in level with line V—V in FIG. 4, FIG. 6 is a perspective view, corresponding to FIG. 2, of a second embodiment of an inventive photometer, FIG. 7 is a perspective view of a microcuvette,.

Figure 1:
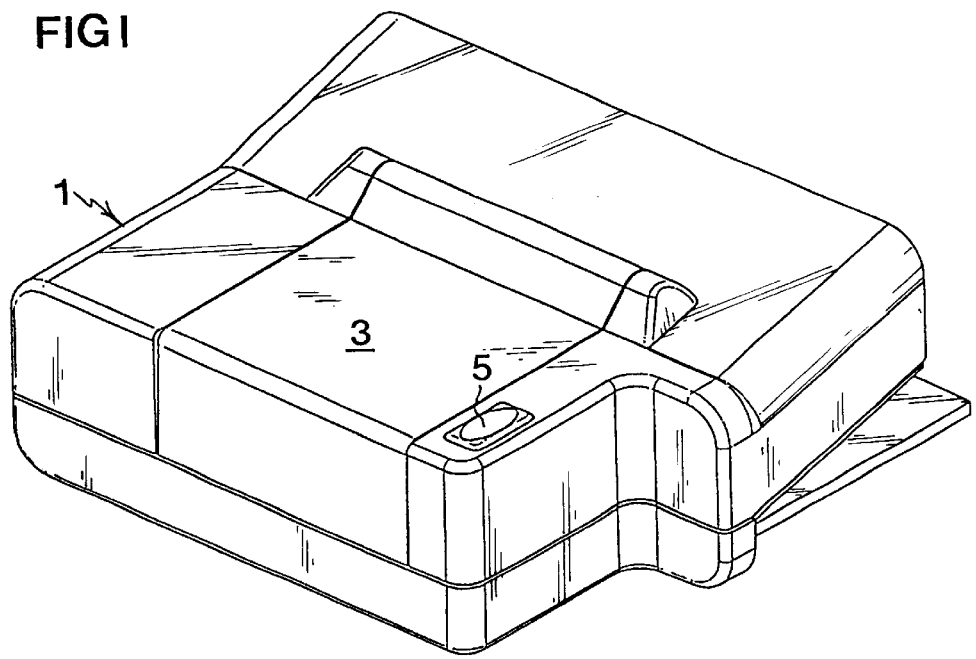
Figure 2:
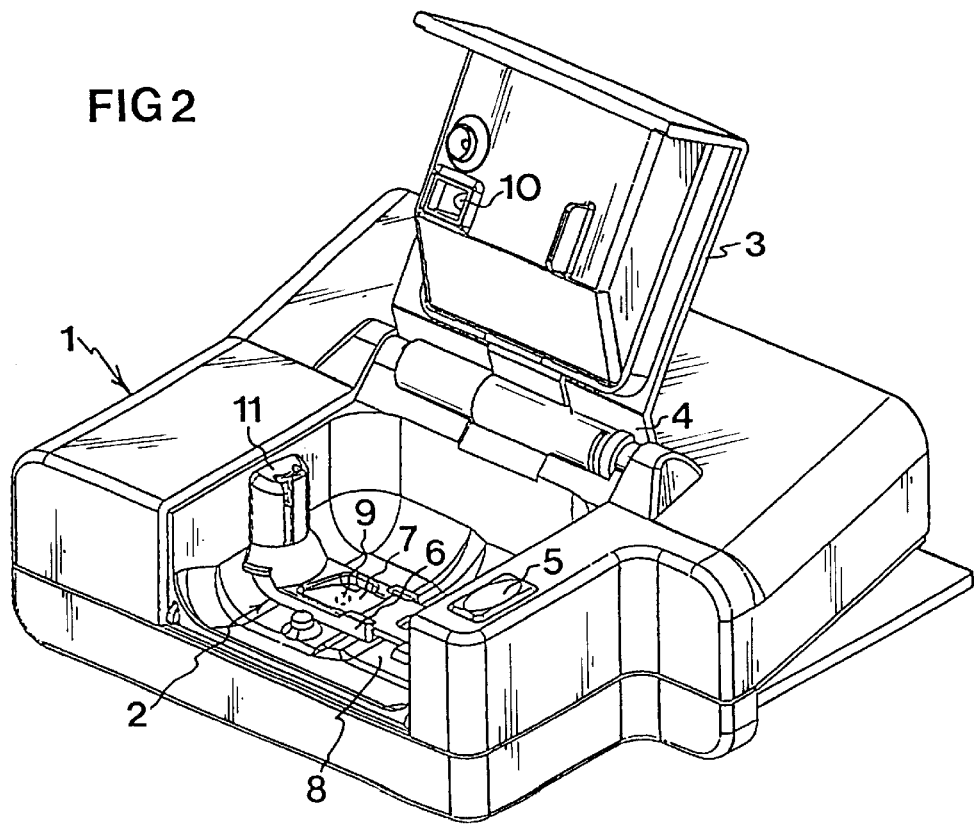
Figure 3:
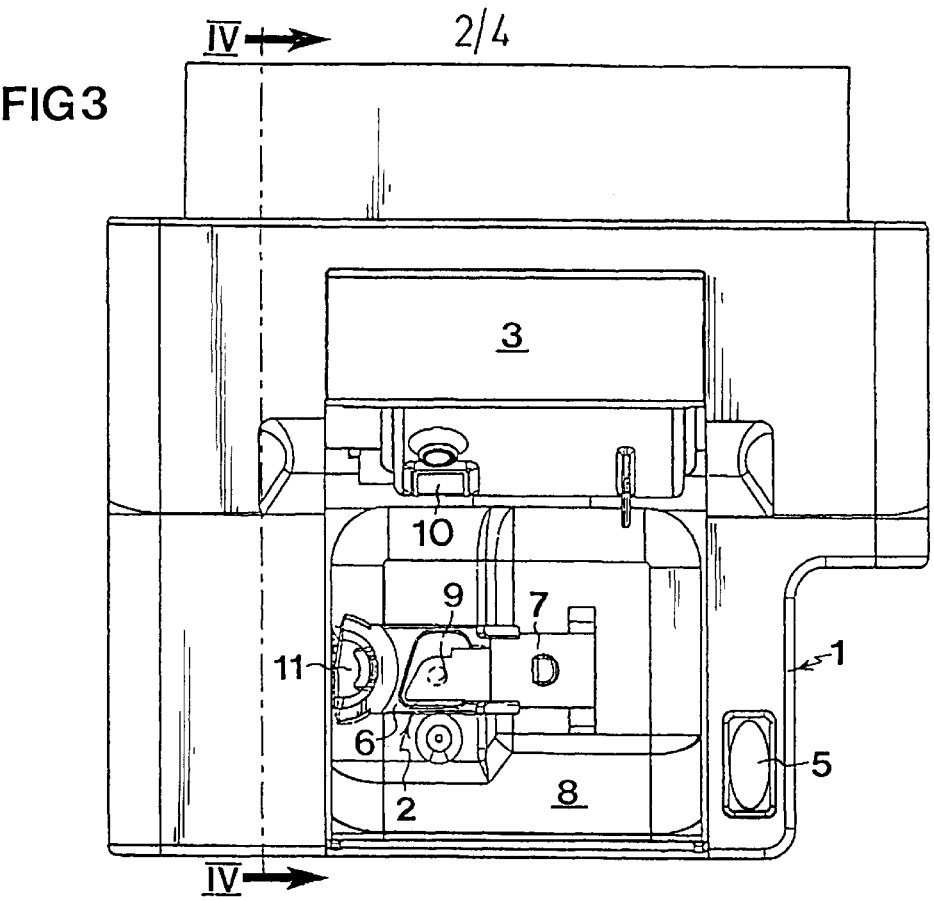
Figure 4:
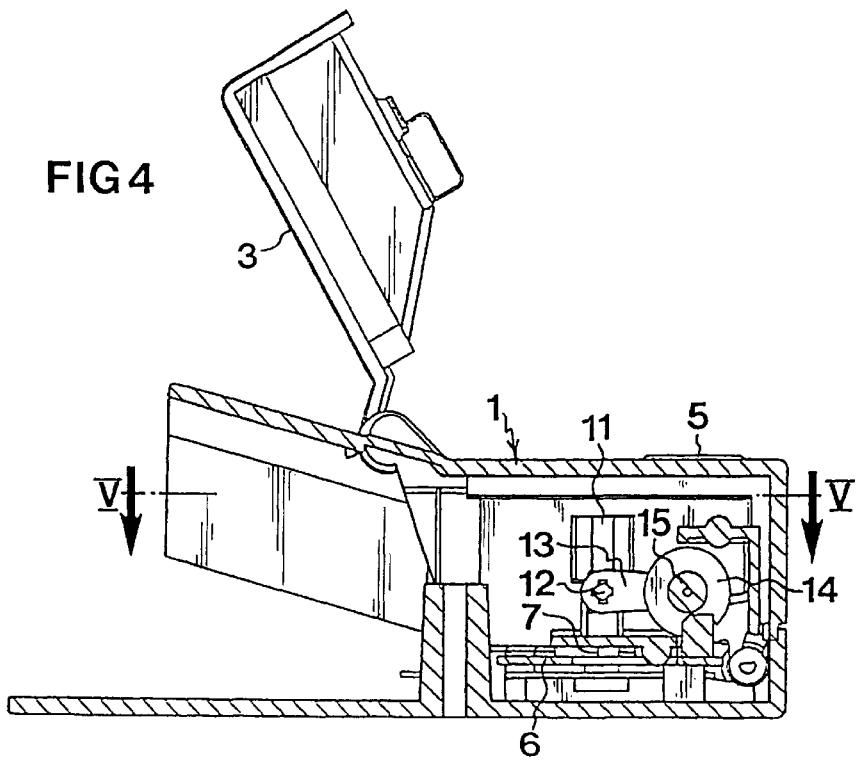
Figure 5:
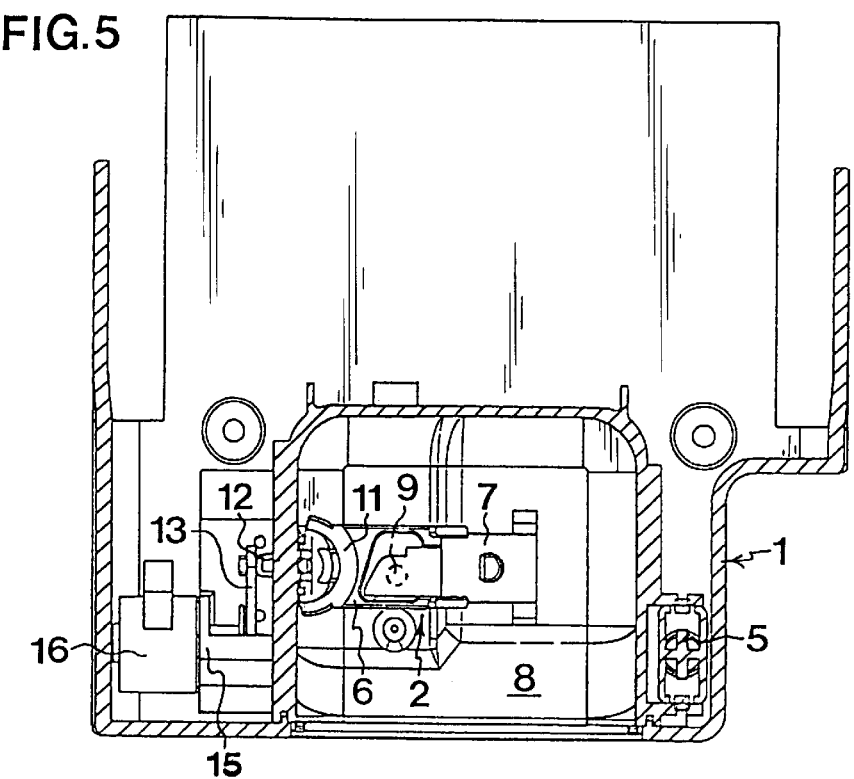

The embodiment of a photometer as illustrated in the drawings in FIGS. 1–5 has a casing 1 with a measuring compartment 2 which is sealable with a cover 3. The cover 3 is pivotally mounted in bearings on a shaft 4 and is held in the closed position by hook members which can be released by pressing a button 5 on the top face of the casing 1, a spring which cooperates with the cover 3 opening the cover to the upwardly pivoted or open position shown in FIG. 2.

A cuvette holder 6 is arranged in the measuring compartment 2. A microcuvette 7 is shown placed in position in the cuvette holder 6 and ready to be measured over a light detector 9 mounted in the bottom 8 of the measuring compartment under the microcuvette 7 arranged in the cuvette holder 6.

The cover 3 consists of two parts, which are telescopically mounted in each other in such manner that the part which in the closed position is the lower one is pressed by spring action against the bottom 8 of the measuring compartment 2, so that the light detector 9 and a source of light 10 in the lower part of the cover 3 take predetermined positions relative to each other after each closing of the cover 3. In the closed position of the cover 3, the source of light 10 and the light detector 9 thus are always positioned at a predetermined distance from each other and in a predetermined orientation relative to each other, which means that the measurements of the photometer can be carried out with excellent repeatability in spite of the movability of the cover 3.

The cuvette holder 6 is pivotally mounted in bearings on a shaft 11, which extends perpendicular to the principal plane of a thin cavity in the microcuvette 7 arranged in the cuvette holder 6. When pivoting the cuvette holder 6 on the shaft 11, the cavity in the microcuvette 7 will thus move in its own plane. The cuvette holder 6 also has an arm 12 which extends on the diametrically opposite side of the shaft 11 to a microcuvette 7 placed in the cuvette holder 6. The free end of the arm 12 is articulated to a first end of a crank 13, whose other end is connected to a crank arm 14, which is fixed to the shaft 15 of a motor 16. The crank arm 14 has in this case the shape of a disc which is concentric with the shaft 15 and is eccentrically connected to the other end of the crank 13.

When the motor 16 drives the crank arm 14 to rotate about the shaft 15, the first end of the crank 13 and thus the free end of the arm 12 are consequently made to oscillate, the cuvette holder 6 making an oscillating motion about the shaft 11 and the microcuvette 7 being vibrated in the principal plane of its cavity.

It is an essential feature that the microcuvette 7 has such a position in the cuvette holder 6 that the sample liquid in the cavity of the microcuvette 7 has the plane of its free liquid surface essentially coinciding with a tangential plane of the shaft 11, i.e. the vibration of the microcuvette 7 in the cuvette holder 6 should occur in a direction which coincides with or at least has a component in the plane of the free liquid surface and is essentially parallel with the principal plane of the cavity. This results in an effective mixing of the sample liquid and the reagent, which accelerates the reaction which causes the transmission change which is decisive of the measurement.

In the actual transmission measurement, the rotation of the motor 16 is stopped. To achieve one and the same measuring position for each measurement, the motor 16, which suitably is a step motor, is adapted to stop the motion of the crank 13 in an area where a displacement of the crank results in a minimum displacement of the cuvette holder 6. This is the case if the stop is made when the arm 12 is positioned either furthest away from or closest to the motor shaft 15.

By vibrating the cuvette holder 6 at such a small amplitude relative to the diameter, which can be a few millimetres, of the bundle of rays directed towards the microcuvette 7 by the source of light 10, that the measurement of the transmission through the microcuvette 7 is not interfered with on any occasion but is continuously executable during the vibration, the transmission change in course of time can be determined. This provides a possibility of determining when the mixing is sufficient for a correct value of the transmission to be obtained.

Figure 6:
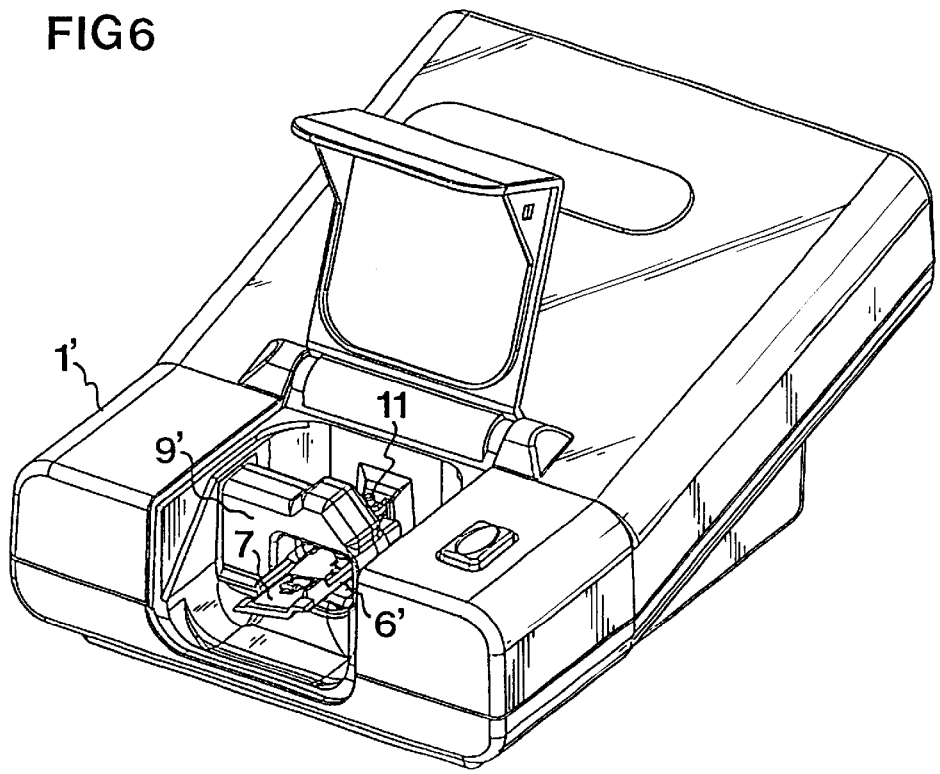

In the second embodiment, shown in FIG. 6, of a photometer according to the invention, the source of light and the light detector are arranged in a measuring bridge 9' which is fixedly mounted in the casing 1' and projects over a cuvette holder 6, which in the same manner as in the embodiment according to FIGS. 1–5 is pivotally mounted on a shaft 11 and made to oscillate by means of a motor. In this case, however, the cuvette holder 6' is tilted through a small angle about a radius to the shaft 11', so that the principal plane of a measuring cavity in a microcuvette 7 placed in the cuvette holder 11' does not extend perpendicularly to the bundle of rays generated in the measuring bridge 9' and directed towards the microcuvette 7. The essential feature is in this case that the deviation from the perpendicular position is not greater than to allow the mixing to occur effectively. For example, a deviation in the order of 10° has been found quite applicable.

To put it in a different way, the principal plane of the measuring cavity makes in this case an acute angle with the plane of oscillation (or in general, with the direction of vibration), while in the embodiment according to FIGS. 1–5 the same principal plane is parallel with the plane of oscillation (and the direction of vibration).

Figure 7:
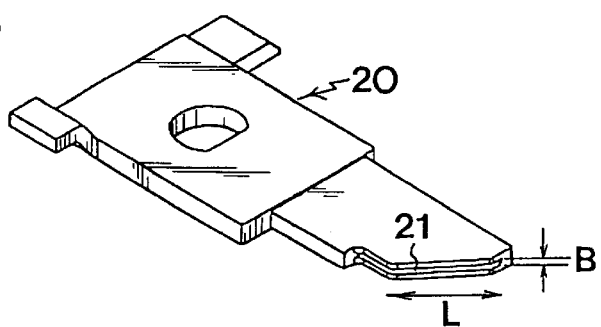
Figure 8:
FIG. 8 is a cross-sectional view of the microcuvette in FIG. 7.

FIGS. 7 and 8 illustrate an example of a microcuvette 20 with a capillary inlet 21. When a sample has been drawn into the cuvette 20, the sample's free interface, which essentially coincides with the opening of the inlet 21, forms an elastic membrane towards the ambient air. It is evident that this free interface is essentially planar and has a greater length L (seen in parallel with the principal plane of the measuring cavity in the microcuvette) than width B (seen perpendicular to said principal plane). The free interface, however, need not necessarily be planar but can be more or less bent, in which case the plane of the interface is to be understood as an average plane of the interface.

Figure 9:
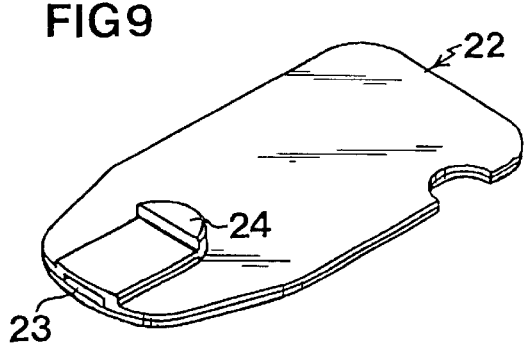
FIG. 9 is a perspective view of a microcuvette with two cavities.
Figure 10:
FIG. 10 is a cross-sectional view of the microcuvette according to FIG. 9.

Correspondingly, two elastic membranes form towards air in the microcuvette 22 illustrated in FIGS. 9 and 10, which has a capillary inlet 23 and a cavity 24 having a greater depth, said cavity being essentially non-capillary.

The agitation according to the invention can be exemplified as follows:

The agitation was studied as a function of cavity depth and beat frequency. Cuvettes of the same design were used.

| Cavity Depth | Beat Frequency (beats/s) | Comments |
| --- | --- | --- |
| 150 µm | 60 | no agitation |
| 130 µm in measuring eye/400 µm outside | 60 | agitation in 400 µm no agitation in 130 µm |
| 130 µm in measuring eye/400 µm outside | 30 | no agitation |
| 300 µm | 60 | no agitation |
| 300 µm | 30 | no agitation |
| 500 µm | 60 | good agitation |
| 500 µm | 30 | no agitation |
| 700 µm | 60 | good agitation |

The results show that the agitation is dependent on both beat frequency and cavity depth. Thus, good agitation is obtained in a 400-µm-deep cuvette at 60 beats/s but not at 30 beats/s. If the depth of the cavity decreases below 15 beats/s, no agitation occurs.

According to the invention, use is preferably made of a beat frequency between 30 and 60 beats/s. Moreover, the measuring cavity is suitably designed to give the thin layer of sample liquid a liquid depth between 10 µm and 1000 µm, preferably between 400 µm and 600 µm.

The invention is well suited for, for instance, methods that are based on antigen-antibody reactions. An example of such a method is determining p albumin in urine, in which case antibodies against human albumin are made to react with albumin in a urine sample. A predetermined amount of antibodies together with auxiliary substances, if any, such as PEG 6000, are applied in the cuvette cavity and dried. When the sample enters the cuvette cavity, which has a predetermined volume, the reagent is dissolved and albumin, which is present in the urine sample, reacts with the dissolved antibodies and forms aggregates causing turbidity, which can be measured spectrophotometrically and is proportional to the concentration of albumin. A mixing according to the present invention, which is preferably carried out in a photometer of the type described above, is an important condition to obtain a quick and reproducible response.

A person skilled in the art appreciates that the above embodiments of the invention can be modified within the scope of the invention as defined by the appended claims.

Thus, the light detector 9 in the embodiment according to FIGS. 1–5 can be arranged offset from a centre line of the bundle of rays from the source of light 10, i.e. be said to measure the transmission of light from the source of light 10 after scattering in the liquid sample through a predetermined angle.

Alternatively, in the embodiment according to FIGS. 1–5 the distance of light detector 9 from the centre line of the bundle of rays can be adjustable so that after scattering through different angles, the transmission can be determined. The latter can also be achieved if the light detector 9 comprises a plurality of light-detecting elements at different distances from said centre line of the bundle of rays. A corresponding arrangement is, of course, possible in the second embodiment according to the FIG. 6.

Finally it should be emphasized that the photometer can be designed to show, on its display unit, the measured transmission or scattering of light or an absorption value corresponding to the measured transmission. It goes without saying that the photometer can also have a signal output connectable to a printer or the like.

What is claimed is:

1. A photometer for determining the transmission of a liquid sample in a microcuvette (7, 20, 22) having a cavity for a capillary layer of the liquid sample with a free liquid surface extended transversely of the principal plane of the cavity, which is initially prepared with a reagent to achieve a reaction, which affects the transmission of the liquid sample to determine its contents of a predetermined substance, said photometer having a holder (6; 6') for the microcuvette and measuring means (9, 10; 9') for measuring the transmission of a bundle of rays directed towards the microcuvette, characterized in that the cuvette holder (6; 6') is mounted in bearings for vibration in a direction having a component which is positioned in the plane of the free liquid surface and parallel with the principal plane of the cavity, thereby achieving a mixing to accelerate dissolution and reaction.

2. A photometer as claimed in claim 1, wherein said component is a main component of the direction of vibration, i.e. vibration occurs essentially in the plane of the free liquid surface and essentially in parallel with the principal plane of the cavity.

3. A photometer as claimed in claim 1, wherein the cuvette holder (6; 6') is mounted in bearings for oscillation about a shaft (11) which is essentially parallel with the direction of a bundle of rays directed towards the cuvette (7, 20, 22) by the measuring means (9, 10; 9').

4. A photometer as claimed in claim 3, wherein a motor (16) is arranged to drive the oscillation of the cuvette holder (6, 6') via a crank (13).

5. A photometer as claimed in claim 4, wherein, for carrying out the measurement, the motor (16) is adapted to stop the motion of the crank (13) in an area where a displacement of the crank causes a minimum displacement of the cuvette holder (6; 6').

6. A photometer as claimed in claim 1, wherein the cuvette holder (6; 6') is adapted to vibrate at such a small amplitude relative to the diameter of a ray of bundles generated by the measuring means (9, 10; 9') for the measurement of the transmission through the microcuvette (7, 20, 22), that the measurement of the transmission through the microcuvette is continuously executable during vibration.

7. A photometer as claimed in claim 2, wherein the cuvette holder (6; 6') is adapted to vibrate at such a small amplitude relative to the diameter of a ray of bundles generated by the measuring means (9, 10; 9') for the measurement of the transmission through the microcuvette (7, 20, 22), that the measurement of the transmission through the microcuvette is continuously executable during vibration.

8. A photometer as claimed in claim 3, wherein the cuvette holder (6; 6') is adapted to vibrate at such a small amplitude relative to the diameter of a ray of bundles generated by the measuring means (9, 10; 9') for the measurement of the transmission through the microcuvette (7, 20, 22), that the measurement of the transmission through the microcuvette is continuously executable during vibration.

9. A photometer as claimed in claim 4, wherein the cuvette holder (6; 6') is adapted to vibrate at such a small amplitude relative to the diameter of a ray of bundles generated by the measuring means (9, 10; 9') for the measurement of the transmission through the microcuvette (7, 20, 22), that the measurement of the transmission through the microcuvette is continuously executable during vibration.

10. A photometer as claimed in claim 5, wherein the cuvette holder (6; 6') is adapted to vibrate at such a small amplitude relative to the diameter of a ray of bundles generated by the measuring means (9, 10; 9') for the measurement of the transmission through the microcuvette (7, 20, 22), that the measurement of the transmission through the microcuvette is continuously executable during vibration.

* * * * *